United States Patent [19]

Sela et al.

[11] 4,093,607

[45] June 6, 1978

[54] IMMUNOLOGIC CHEMOTHERAPEUTIC AGENTS COMPRISING ANTIGEN BINDING DIMERS COVALENTLY BOUND TO DRUGS

[75] Inventors: Michael Sela; Ruth Arnon, both of Rehovot; Ruth Maron, Tel Aviv, all of Israel; Esther Hurvitz, Potomac, Md.

[73] Assignee: Yeda Research and Development Co., Ltd., Rehovot, Israel

[21] Appl. No.: 689,276

[22] Filed: May 25, 1976

[30] Foreign Application Priority Data

May 27, 1975 Israel .......................................... 47372

[51] Int. Cl.² ................................................ C07G 7/00
[52] U.S. Cl. ............................ 260/112 B; 260/112 R; 424/85; 424/88
[58] Field of Search ........................ 260/112 B, 112 R; 424/85, 88

[56] References Cited

U.S. PATENT DOCUMENTS

| | | | |
|---|---|---|---|
| 3,850,798 | 11/1974 | Sjöquist | 260/112 B UX |
| 3,928,580 | 12/1975 | Fontaine | 260/112 B |
| 3,966,898 | 6/1976 | Sjöquist et al. | 260/112 B |
| 3,995,018 | 11/1976 | Sjöquist | 260/112 B X |

OTHER PUBLICATIONS

Scientific American, vol. 216, pp. 81–90 (1967), Porter et al.
Scientific American, vol. 223, pp. 34–42 (1970), Edelman.
Cancer Research, vol. 35, pp. 1175–1186, Hurwitz et al., 1975 (May).

*Primary Examiner*—Howard E. Schain
*Attorney, Agent, or Firm*—Paul L. Sabatine; Thomas E. Ciotti; Edward L. Mandell

[57] ABSTRACT

Chemotherapeutic agents comprising an antigen binding dimer derived from an immunoglobulin covalently bound to a drug are disclosed. The dimer and drug are bound, while preserving both the antibody activity of the dimer and the pharmacological activity of the drug.

17 Claims, 3 Drawing Figures

IMMUNOLOGIC CHEMOTHERAPEUTIC AGENTS COMPRISING ANTIGEN BINDING DIMERS COVALENTLY BOUND TO DRUGS

FIELD OF THE INVENTION

This invention pertains to both novel and useful chemotherapeutic compositions of matter. In preferred embodiments, the invention relates to an antigen binding dimer covalently bonded to an anti-cancer drug. The chemotherapeutics are useful for the management of neoplastic diseases.

BACKGROUND OF THE INVENTION

Many chemotherapeutic anti-cancer agents, known to the prior art in *Pharmaceutical Sciences* by Remington, 15th Ed., pages 1074 to 1086, 1975, published by the Mack Publishing Co., Easton, Pa., are indicated as having a certain degree of usefulness for the management of neoplastic diseases, particularly against neoplastic cells. However, the use of these agents is often limited because of their detrimental toxic effects on normal tissues. The effectiveness of these anti-tumor agents can be improved by methods altering their distribution in the body to increase their local concentration at the tumor cell site. In this manner, the selectivity of their chemotherapeutic effect for tumor cells may be enhanced in the body.

For example, the prior art has reported that some anti-tumor drugs may be bound convalently to macromolecules without concomitant loss of activity, and that non-covalent complexes or mixtures of the drug and anti-tumor antibodies may be more efficient than the drug alone. Also, it has been shown as reported in *Cancer Research*, Vol 35, pages 1175 to 1181 and 1182 to 1186, 1975, that the potent anti-tumor antibiotics daunomycin and adriamycin can be linked covalently to immunoglobulins with retention of their activities. The cytotoxic activity of these drug-antibody conjugates as tested in vitro on tumor and normal cell cultures was found to be similar to that of the free drug, and a significant amount of antibody activity was retained. When conjugates of daunomycin with immunoglobulines directed against either of two lymphoid tumors were tested for their toxic effects on various tumor target cells, it was found that the drug preferentially affected those target cells which the antibodies could recognize.

OBJECTS AND SUMMARY OF THE INVENTION

Accordingly, it is an object of the present invention to provide a composition of matter comprising a drug covalently bound to an antibody selective or specific to a tissue or cell antigen.

Another object of the invention is to provide a composition of matter comprising an antigen binding dimer derived from immunoglobulins containing anti-tumor antibodies covalently bound to an anti-tumor agent.

Yet another object of the invention is to provide a composition of matter comprising an antigen binding dimer covalently bound to a drug which composition is indicated for altering the distribution of the drug in a host.

Still yet another object of the invention is to provide a method for altering the distribution of anti-tumor drugs in a host to increase their concentration at the tumor cell site.

The invention in its most specific aspect concerns fragment antigen binding dimers derived by the enzymatic digestion of immunoglobulins containing anti-tumor antibodies as covalent carriers for anti-tumor agents.

Other objects, features and advantages of the invention will be more apparent to those versed in the art from the detailed description of this specification, taken in conjunction with the figures and the accompanying claims.

DETAILED DESCRIPTION OF THE DISCLOSURE

Figure 1:
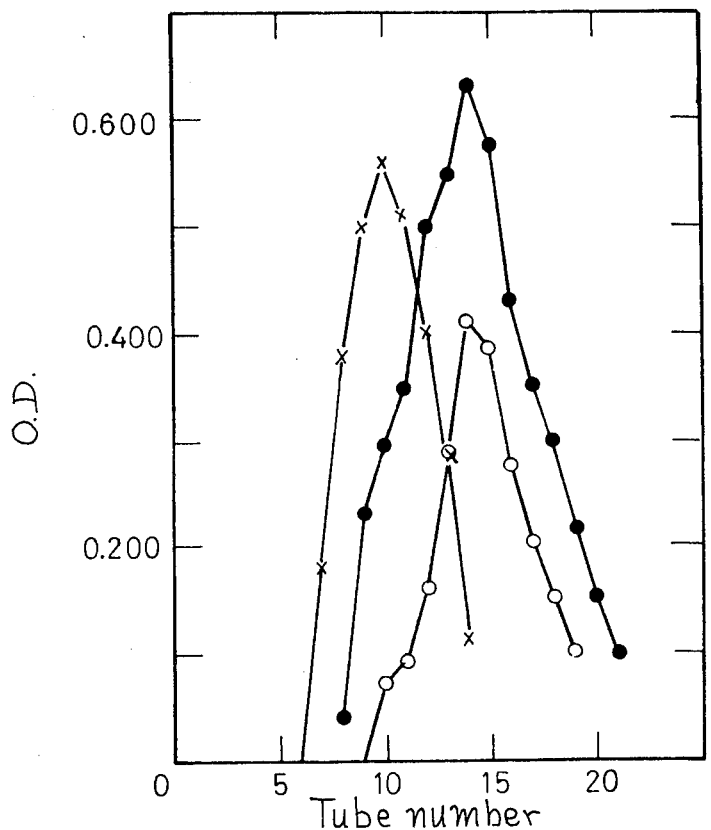

In accordance with the practice of the present invention, it has now been found that drug-antibody conjugates can be provided that are designed to reach the target cell as specifically as possible. In accordance with the practice of the invention, it is most desirable that whatever has not been attached to the cellular antigen, should be removed from the circulation as quickly as possible. For the purpose of this invention, the "fragment antigen binding dimer", also identified as $(Fab')_2$, derived from an antibody, is preferred to an intact antibody molecule which still possesses the "fragment crystallizable", also identified as the Fc fragment, since the half-life of the $(Fab')_2$ in the blood stream is much shorter than that of the intact immunoglobulin. The use of antibodies for local delivery of drugs for therapeutic purposes may involve heterologous antibodies which being immunogenic, might elicit unfavorable reactions. The Fc is the most immunopotent region of an immunoglobulin, and its removal leads to a molecule, the Fab' dimer, which is less immunogenic, even though it most probably will still elicit antibodies capable of reacting with determinants on Fab'.

According to the present invention, as described supra, there can be provided covalent conjugates of drugs with Fab' dimers derived from immunoglobulins. The drugs can be selected from known drugs including, in presently preferred embodiments, alkylating, antimetabolites, antibiotic and alkaloids. Exemplary anti-tumor drugs embraced by these classes include daunomycin, adriamycin, methotrexate, mithramycin, cytosine, arabinoside and 6-azauridine. These drugs are described in *The Pharmacological Basis of Therapeutics*, edited by Goodman, et al, 5th Ed., Section XV, pages 1248 to 1308, 1975, published by the Macmillan Co., New York. In operation, the covalent conjugate will be used in an amount needed that contains sufficient drug to elicit the desired pharmacological response. Generally, this amount will correspond to the amount disclosed in the text for the respective drug. The dose administered will of course vary with the particular conjugate used due to varying potency, the route of administration, the size of the recipient and the nature of the disease being treated. Exemplary of an operable does is for 2.5 μg to 5 mg per kg of mouse. Those versed in the art can of course use smaller or larger amounts predicated on the need and the desired beneficial result.

The antigen binding dimers used for the invention are derived by the proteolytic enzyme digestion of an immunoglobulin containing an antibody specific to a tissue or cell antigen and in presently preferred embodiments, an anti-tumor antibody specific to a tumor antigen. Generally, the dimers can be derived from immunoglobin preparations isolated from cells of blood, cells of tissues and cells of bone marrow. Exemplary dimers can be obtained from immunoglobulin preparations specific to various tumors, including tumors associated with acute lymphatic leukemia; acute myelocytic leukemia; lymphoma; tumors of the breast, bladder and testes; osteogenic sarcoma, soft tissue sarcoma and similar malignant growth types. The presently preferred proteolytic enzyme used for degrading the immunoglobulin is pepsin.

The following description is merely illustrative of mode and manner of carrying out the present invention, and it should not be considered as limiting the scope of the invention in any way, as these embodiments and other equivalents thereof will become apparent to those versed in the art in the light of the present disclosure and the accompanying claims.

DETAILED DESCRIPTION OF EMBODIMENTS

According to the invention, there were prepared covalent conjugates of daunomycin antibiotic with Fab' dimers derived from immunoglobulins isolated from an anti-lymphoma antiserum. The covalent conjugates were investigated for their cytotoxic capacity in vitro by conventional procedures as described below. Similar results may be expected in warm blooded animals such as mice, rats, rabbits, guinea pigs and the like predicated on reported procedures that indicate various macromolecules have been shown to localize in tumor cells and were therefore suggested as carriers for cytotoxic drugs; see for example Isliker, et al, in *Chemotherapy of Cancer*, pages 278 to 288, 1969, published by Elsevier Publishing Co., Amsterdam; and, Hurwitz, et al, *Cancer Res.*, Vol. 35, pages 1175 to 1181, 1975, and the references cited therein.

The chemicals and reagents used to prepare the covalent conjugates were obtained from various sources. The antibiotic daunomycin hydrochloride was obtained as cerubidine from Specia of Paris, France. The compound 5-[$^3$H] Uridine having a specific activity of 25 c/mM and $^{125}$I were obtained from Radiochemical Center of Amersham, England. Sodium periodate and sodium borohydride were obtained from British Drug House of Poole, England. Biogel $^{(R)}$ P-60 was obtained from Bio-rad of Los Angeles, California. Porapak$^{(R)}$ Q, 50-80 mesh was obtained from Waters Associates of Boston, Massachusetts, and Sephadex$^{(R)}$ G-200 was obtained from Pharmacia of Uppsala, Sweden.

The tumor cells and antisera used were procedures as follows: tumor cells, a lymphoma (Yac) Maloney virus induced and transferred in A/J mice, according to Klein, et al, in *J. Natl. Cancer Inst.*, Vol. 32, pages 547 to 568, 1964. Antiserum to bovine serum albumin (BSA) was produced in rabbits by subcutaneous injections of 2 mg BSA emulsified in complete Freund's adjuvant, twice at weekly intervals. Antiserum to rabbit (Fab')$_2$ was produced alike in goats. Antisera to Yac cells were prepared by 5 intravenous injections of 10$^8$ cells at 5 day intervals. The immunoglobulin fractions of these antisera were prepared by precipitation with ammonium sulfate at 33% saturation. Any anti-tumor IgG or (Fab')$_2$ used in vivo was absorbed with normal cells of the spleen, thymus, liver and erythrocytes. The absorption was repeated in steps each time for 30' at 37° C until no residual in vitro activity towards normal spleen was obtainable.

The pharmacological activity of daunomycin was measured primarily by the inhibition of cellular RNA synthesis. A procedure for measuring the inhibition is disclosed by Hurwitz, et al in *Cancer Research*, Vol. 35, pages 117 to 1181, 1975.

The fragment antigen binding dimer, (Fab')$_2$ were prepared as follows: immunoglobulin fractions were digested by pepsin at an enzyme to protein ratio of 1/50 (w/w), in 0.1 M sodium acetate buffer, pH 4.5 for 16 hours at 37° C. The digestion was stopped by neutralization of pH 7.4 and the reaction mixture was then dialyzed extensively against phosphate buffered saline (PBS).

The iodination of IgG of Goat Anti-rabbit (Fab')$_2$ was performed as follows: the immunoglobulin fraction from goat antiserum against rabbit (Fab')$_2$ was iodinated according to McConahey, et al, *Int. Arch. Allergy*, Vol. 29, page 185, 1966. The specific activity of the preparation was 1 × 10$^8$ cpm/mg protein.

The covalent binding of daunomycin to (Fab')$_2$ preparations was carried out as follows: the linking of daunomycin to (Fab')$_2$ was performed by binding sodium periodate oxidized drug to the free amino groups of the protein, forming a Schiff base. These bonds were then stabilized by reduction with sodium borohydride. Details for carrying out this procedure are similar to those reported by Erlanger, et al, in *Proc. Natl. Acad. Sci., U.S.*, Vol. 52, pages 68 to 74, 1964; and as disclosed by Hurwitz, et al, in *Cancer Res.*, Vol. 35, pages 1175 to 1181, 1975. The extent of substitution can be varied in different preparations from at least one mole of drug per mole of dimer and usually from 2 to 10 moles drug per mole antibody, and the like.

The measurement of antibody activity was performed as follows: the antibody activity of the (Fab')$_2$ from anti-BSA was measured by the BSA-T$_4$ bacteriophage system as disclosed by Haimovich, et al, in *Biochem. Biophys. Acta.*, Vol. 207, pages 115 to 124, 1970. The anti-Yac (Fab')$_2$ was measured by its binding to Yac tumor cells. Yac cells (2 × 10$^6$) in 0.2 ml minimal essential medium (Mem) containing 10% decomplemented fetal calf serum (FCS) were incubated with various concentrations of whole IgG or (Fab')$_2$ from anti-Yac sera for 1 hour at 0° C on a shaker. Following this incubation period, the cells were centrifuged (at 1000 × g) and washed three times with Mem. After the washings, the cells were dispersed in 0.1 ml medium supplemented with 10% FCS and a 5 mg/ml solution of $^{125}$I-IgG of goat anti-rabbit (Fab')$_2$ was added to each tube. The mixture was reincubated under the same conditions as mentioned above, followed by centrifugation and three washes. After washing, the cells were dispersed in 0.5 ml Mem and the bound radioactivity counted in an autogamma counter, available from the Hewlett-Packard Corp., Palo Alto, California.

The preparation of (Fab')$_2$ from anti-BSA and anti-Yac immunoglobulins was performed as follows: ammonium sulfate precipitated IgG fractions of anti-BSA and anti-Yac were digested by pepsin as described above. A sample of each digest was applied to a column (27 × 2 cm) of Sephadex G-200 and compared to whole (undigested) IgG run on the same column as seen in FIG. 1. The pepsin digestion was carried out to completion, as indicated by the finding that the reduction, followed by alkylation, of the (Fab')$_2$ preparation yielded exclusively that Fab' monomer, as monitored on the same Sephadex G-200 column. In FIG. 1, the preparation of anti-Yac (Fab')$_2$ is indicated by clear (O) and anti-BSA (Fab')$_2$ by dark (•). The Figure also shows gel filtration on Sephadex G-200 (23 × 2 cm) of the (Fab')$_2$ fractions in relation to whole IgG (X).

The pharmacological activity of protein-bound drug was ascertained as follows: the inhibition of [$^3$H] Uridine incorporation was used to quantitate drug activity. The activity of free daunomycin and two different preparations of daunomycin bound to (Fab')₂ is described in Table I immediately below. The results demonstrate that the covalent binding of daunomycin to (Fab')₂ did not cause any loss in the pharmacological activity of the drug.

TABLE 1

The Pharmacological Activity Of Daunomycin Covalently Bound To (Fab')₂

| Daunomycin μg/ml | % Inhibition of [³H] uridine incorporation | | |
|---|---|---|---|
| | Daunomycin | Daunomycin-anti-BSA(Fab')₂ | Daunomycin-anti-Yac(Fab')₂ |
| 13 | 43 | 58 | 56 |
| 33 | 64 | 74 | 80 |
| 66 | 80 | 84 | 85 |

Figure 2:
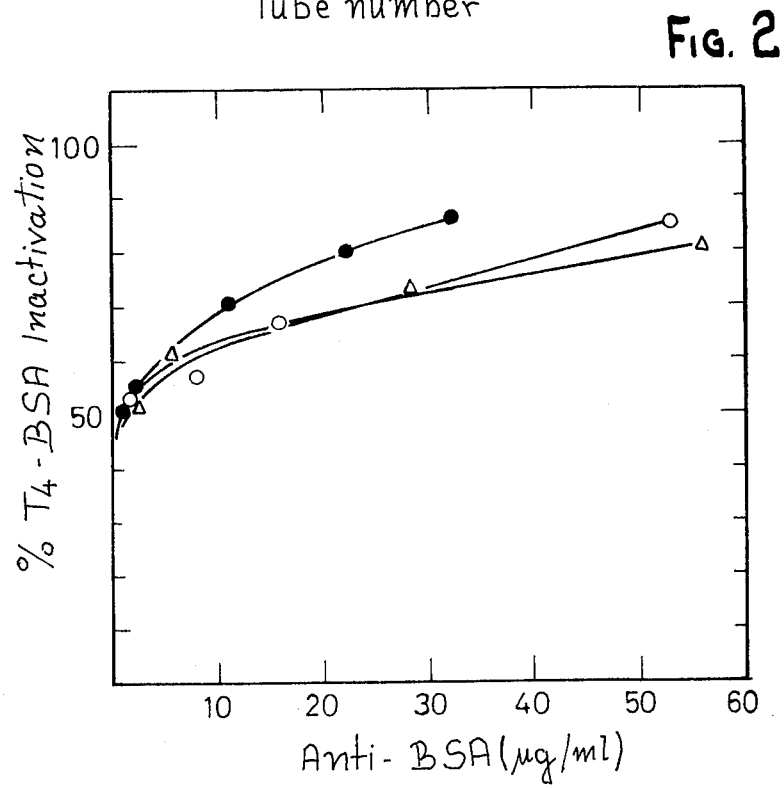

The antibody activity of daunomycin substituted (Fab')₂ is seen in FIG. 2. FIG. 2 shows the antibody activity of (Fab')₂ anti-BSA as measured by percent inactivation of BSA-T₄ bacteriophage, according to the procedure reported by Haimovich, et al, in Biochim. Biophys. Acta., Vol. 207, pages 115 to 124, 1970. As can be seen in FIG. 2, there is very little reduction in the antibody activity of the conjugate when compared to the unsubstituted (Fab')₂. The antibody activity is retained alike in a poorly substituted preparation (4 M/M) or a highly substituted preparation (14 M/M). In FIG. 2, anti-BSA (Fab')₂ is indicated by dark (•), daunomycin-anti-BSA (Fab')₂ 15 M/M by (Δ), and daunomycin-anti-BSA (Fab')₂ 4 M/M by clear (O).

Figure 3:
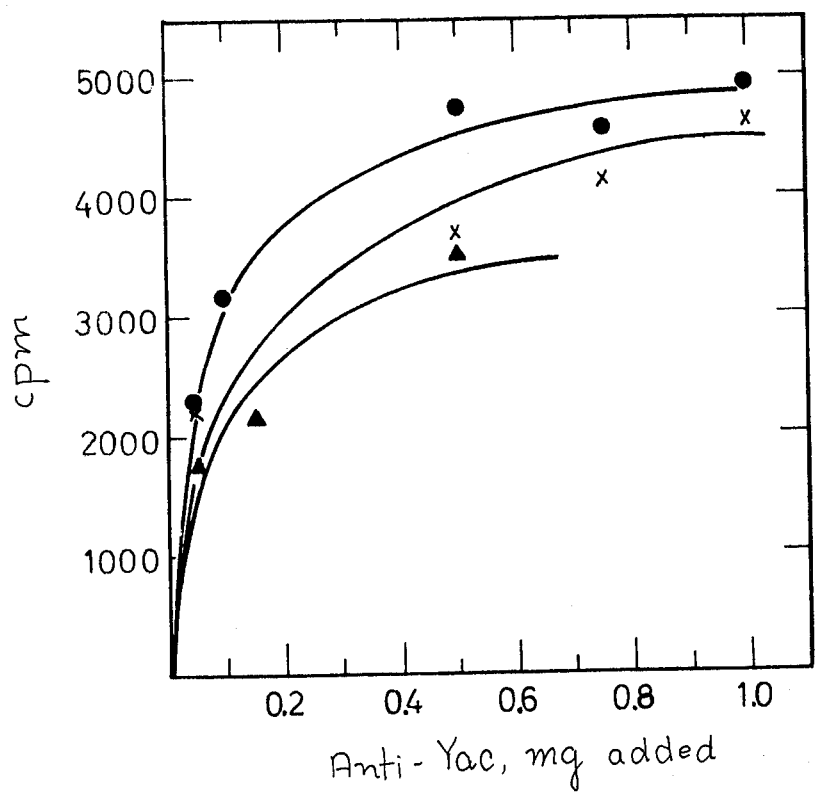

The activity of the (Fab')₂ from anti-Yac as measured by its binding activity to the target cells is depicted in FIG. 3. It can be noted that the antibody activity of the daunomycin - (Fab')₂ conjugate, measured by the binding of iodinated goat anti-rabbit (Fab')₂ is decreased by 23-27% compared to whole IgG or to non-substituted (Fab')₂ but a significant binding capacity (over 70%) is retained. The observed reduction in the binding of (Fab')₂ to the cells relative to whole IgG may be due to the preparation procedure. In FIG. 3, the binding of anti-Yac IgG is indicated by (O), (Fab')₂ by (X) and daunomycin (Fab')₂ by (Δ) to Yac cells was measured by a double binding technique with ¹²⁵I labeled goat anti-rabbit (Fab')₂.

The specific cytotoxicity of daunomycin-anti-Yac (Fab')₂ conjugates is determined as follows: the advantages of daunomycin bound to specific anti-Yac (Fab')₂ rather than to unrelated antibodies, anti-BSA (Fab')₂, was tested in vitro by exposure of the tumor cells to drug-bound (Fab')₂ fractions, or the free drug, for only 5 minutes. The cells were then washed to remove reactants unbound to the cells, and the toxicity of the daunomycin remaining in contact with the cells was assessed by the inhibition of [³H] uridine incorporation. As can be seen from the results as set forth in Table II immediately below, daunomycin-anti-Yac was twice as active as the unrelated (Fab')₂ of anti-BSA or the free drug.

TABLE II

Specific Cytotoxicity of Daunomycin Linked To Anti-Yac (Fab')₂

| Yac cells incubated with | % Inhibition of [³H] uridine incorporation |
|---|---|
| Daunomycin-anti-Yac | 60, 56 |
| Daunomycin-anti-BSA | 36, 34 |
| Free daunomycin | 33, 16 |

Similar results can be obtained by repeating the above procedures with other anti-tumor drugs including adriamycin, methotrexate, mithramycin, cytosine arabinoside, 6-azauridine, and the like, covalently bound to Fab' dimers according to the spirit of the invention. These drug are known to the art and they are active against a wide range of tumors in animals as reported by Frei in Cancer, Vol. 30, pages 1656 to 1661, 1972; and O'Bryan, et al, in Cancer, Vol. 32, pages 1 to 8, 1973.

It is clear from the above that Fab' dimers bonded to anti-tumor drugs are characterized by an enhanced and improved activity against certain types of tumors, and that these are concentrated at the location of the tumor. And, while there has been described and pointed out the fundamental novel features of the invention as applied to presently preferred embodiments, those skilled in the art will appreciate that various modifications, changes and omissions can be made in the procedures illustrated and described without departing from the spirit of the invention.

We claim:

1. A composition of matter comprising an antigen binding dimer containing an anti-tumor antibody specific to a tumor antigen, said dimer covalently bonded to an anti-cancer drug through a functional group on the dimer that is nonessential for antibody activity of the dimer, and through a functional group on the drug that is nonessential for the pharmacological activity of the drug, thereby preserving both the antibody activity of the dimer and the pharmacological activity of the drug.

2. The composition of matter according to claim 1 wherein the drug is a pharamceutically active antibiotic.

3. The composition of matter according to claim 1 wherein the drug is a pharmaceutically active antimetabolite.

4. The composition of matter according to claim 1 wherein the drug is a pharamceutically active alkaloid.

5. The composition of matter according to claim 1 wherein the drug is a pharmaceutically active alkylating drug.

6. The composition of matter according to claim 1 wherein the drug is a chemotherapeutic selected from the group consisting of daunomycin, adriamycin, methotrexate, mithramycin, cytosine arabinoside, and 6-azauridine.

7. The composition of matter according to claim 1 wherein at least one mole of drug is covalently bonded to a mole of dimer.

8. The composition of matter according to claim 1 wherein the antibody has specificity to a tumor antigen derived from cells of blood.

9. The composition of matter according to claim 1 wherein the antibody has specificity to tumor antigens from cells derived from bone marrow.

10. The composition of matter according to claim 1 wherein the antibody has specificity to tumor antigens from cells derived from tissue.

11. The composition of matter according to claim 1 wherein the dimer is derived from anti-Yac antibodies.

12. A process for the preparation of an anti-tumor drug covalently bonded to an antigen binding dimer, which process comprises the steps of oxidizing the drug with an oxidizing agent, bonding the oxidized drug to the dimer, and then stabilizing the bond formed by reduction with a reducing agent, to yield an antigen binding dimer possessing antibody activity bonded to a drug possessing pharmacological activity.

13. The process for the preparation of an anti-tumor drug covalently bonded to an antigen binding dimer according to claim 12 wherein the oxidizing agent is sodium periodate, the oxidized drug is bonded to a free amino group of the dimer forming a Schiff's base, and the reducing agent is sodium borohydride.

14. A process for preparing a pharmaceutical composition of matter comprising an antigen binding dimer formed by the proteolytic enzyme digestion of an immunoglobulin containing an anti-tumor antibody specific to a tumor antigen, said dimer covalently bound to an anti-cancer drug through a functional group on the dimer that is nonessential for the antibody activity of the dimer, and through a functional group on the drug that is nonessential for the pharmacological activity of the drug, and wherein said process comprises the steps of oxidizing the drug with an oxidizing agent, binding the oxidized drug to a free functional group on the dimer, and stabilizing the bonds formed by reduction with a reducing agent thereby producing an antigen binding dimer possessing both the antibody activity of the dimer and the pharmacological activity of the drug.

15. The process for preparing the composition of matter comprising the antigen binding dimer containing an anti-tumor antibody covalently bound to an anti-cancer drug according to claim 14 wherein the oxidizing agent is sodium periodate, the oxidizing drug is bound to a free amino group of the dimer by a Schiff's base, and the reducing agent is sodium borohydride.

16. The process for preparing the composition of matter according to claim 14 wherein the drug is a chemotherapeutic selected from the group consisting of alkylating, antibiotic, antimetabolic, and alkaloid drugs, and wherein at least one mole of drug is covalently bonded per mole of antigen binding dimer.

17. A composition of matter comprising an antigen binding dimer formed from an immunoglobulin selective to a tissue or cell antigen, said dimer covalently bound to a pharmaceutically acceptable drug through a functional group on the dimer that is nonessential for antibody activity, and through a functional group on the drug that is nonessential for the pharmaceutical activity of the drug for simultaneously preserving the antibody activity of the dimer, and the pharmacological activity of the drug.

* * * * *